(12) United States Patent
McCarthy et al.

(10) Patent No.: US 8,870,871 B2
(45) Date of Patent: Oct. 28, 2014

(54) BIODEGRADABLE BONE PLATES AND BONDING SYSTEMS

(75) Inventors: Stephen McCarthy, Tyngsboro, MA (US); Jeffrey Weinzweig, Boston, MA (US)

(73) Assignee: University of Massachusetts Lowell, Lowell, MA (US)

( * ) Notice: Subject to any disclaimer, the term of this patent is extended or adjusted under 35 U.S.C. 154(b) by 394 days.

(21) Appl. No.: 11/787,076

(22) Filed: Apr. 13, 2007

(65) Prior Publication Data

US 2008/0234754 A1   Sep. 25, 2008

Related U.S. Application Data

(60) Provisional application No. 60/885,303, filed on Jan. 17, 2007.

(51) Int. Cl.

| | |
|---|---|
| *A61B 17/56* | (2006.01) |
| *A61B 17/80* | (2006.01) |
| *A61L 31/04* | (2006.01) |
| *C08L 67/04* | (2006.01) |
| *A61L 2/10* | (2006.01) |
| *A61L 24/04* | (2006.01) |
| *C09J 167/04* | (2006.01) |
| *A61L 31/14* | (2006.01) |
| *A61L 27/16* | (2006.01) |
| *A61L 2/20* | (2006.01) |
| *A61L 2/08* | (2006.01) |
| *A61B 17/00* | (2006.01) |
| *C08L 67/00* | (2006.01) |

(52) U.S. Cl.
CPC ........... *A61B 17/8085* (2013.01); *A61L 31/041* (2013.01); *A61B 2017/00004* (2013.01); *C08L 67/04* (2013.01); *A61L 2/10* (2013.01); *A61L 24/043* (2013.01); *A61L 2202/18* (2013.01); *C09J 167/04* (2013.01); *A61B 17/00491* (2013.01); *A61L 31/148* (2013.01); *A61L 27/16* (2013.01); *A61L 2202/24* (2013.01); *C08L 67/00* (2013.01); *A61L 2/206* (2013.01); *A61L 2/087* (2013.01); *A61L 2/081* (2013.01)
USPC ........................................... 606/76; 606/298

(58) Field of Classification Search
USPC ............... 606/70, 76, 77, 280, 281, 283, 298, 606/908, 910, 300
See application file for complete search history.

(56) References Cited

U.S. PATENT DOCUMENTS

| | | | |
|---|---|---|---|
| 3,997,138 A | | 12/1976 | Crock et al. |
| 4,035,334 A | * | 7/1977 | Davydov et al. ........... 424/78.06 |

(Continued)

FOREIGN PATENT DOCUMENTS

| | | |
|---|---|---|
| EP | 0 460 439 A2 | 12/1991 |
| JP | S63-186642 A | 8/1988 |

(Continued)

OTHER PUBLICATIONS

"Blend": Webster's Online Dictionary, www.mirriam-webster.com, Apr. 1, 2010.*

(Continued)

*Primary Examiner* — Christian Sevilla
(74) *Attorney, Agent, or Firm* — Nutter McClennen & Fish LLP

(57) ABSTRACT

The invention relates to novel internal fixation devices, such as bone plates, generally and novel craniomaxillofacial bone plates more specifically and systems for bonding the same. More specifically, the invention relates to bone plates made of a polymer blend of (poly)lactic acid and Ecoflex as well as a novel hot-melt adhesive polymer blend of the same material.

12 Claims, 7 Drawing Sheets

(56) References Cited

U.S. PATENT DOCUMENTS

| | | | |
|---|---|---|---|
| 4,164,794 A | 8/1979 | Spector et al. | |
| 4,661,530 A * | 4/1987 | Gogolewski et al. | 521/137 |
| 4,683,878 A | 8/1987 | Carter | |
| 4,968,317 A | 11/1990 | Tormala et al. | |
| 4,988,358 A | 1/1991 | Eppley et al. | |
| 5,092,883 A | 3/1992 | Eppley et al. | |
| 5,139,527 A * | 8/1992 | Redl et al. | 623/66.1 |
| 5,163,960 A * | 11/1992 | Bonutti | 128/898 |
| 5,216,050 A * | 6/1993 | Sinclair | 524/108 |
| 5,342,395 A | 8/1994 | Jarrett et al. | |
| 5,373,860 A | 12/1994 | Catone | |
| 5,578,046 A | 11/1996 | Liu et al. | |
| 5,626,611 A | 5/1997 | Liu et al. | |
| 5,662,710 A | 9/1997 | Bonutti | |
| 5,717,030 A | 2/1998 | Dunn et al. | |
| 5,725,529 A | 3/1998 | Nicholson et al. | |
| 5,735,875 A | 4/1998 | Bonutti et al. | |
| 5,853,746 A | 12/1998 | Hunziker | |
| 5,883,199 A * | 3/1999 | McCarthy et al. | 525/437 |
| 5,954,724 A | 9/1999 | Davidson | |
| 6,059,817 A | 5/2000 | Bonutti et al. | |
| 6,214,008 B1 | 4/2001 | Illi | |
| 6,339,913 B1 * | 1/2002 | Leon Fong et al. | 53/425 |
| 6,365,680 B1 * | 4/2002 | Edgington et al. | 525/450 |
| 6,548,569 B1 | 4/2003 | Williams et al. | |
| 6,632,503 B1 | 10/2003 | Shikinami et al. | |
| 6,787,613 B2 * | 9/2004 | Bastioli et al. | 525/411 |
| 7,455,674 B2 | 11/2008 | Rose | |
| 7,717,946 B2 | 5/2010 | von Oepen et al. | |
| 8,029,575 B2 | 10/2011 | Borden | |
| 8,287,909 B2 | 10/2012 | Martin et al. | |
| 2002/0022843 A1 | 2/2002 | Michelson | |
| 2004/0030341 A1 * | 2/2004 | Aeschlimann et al. | 606/72 |
| 2004/0030342 A1 | 2/2004 | Trieu et al. | |
| 2004/0143072 A1 * | 7/2004 | Lewis et al. | 525/417 |
| 2005/0201974 A1 | 9/2005 | Schestopol et al. | |
| 2005/0273165 A1 * | 12/2005 | Griffiths et al. | 623/16.11 |
| 2006/0122604 A1 | 6/2006 | Gorhan et al. | |
| 2006/0252981 A1 | 11/2006 | Matsuda et al. | |

FOREIGN PATENT DOCUMENTS

| | | |
|---|---|---|
| JP | H02-276818 A | 11/1990 |
| JP | H05-339557 A | 12/1993 |
| JP | H07-502069 A | 3/1995 |
| JP | H08-92359 A | 4/1996 |
| JP | H11-192299 A | 7/1999 |
| JP | 2004-512090 A | 4/2004 |
| JP | 2005-330458 A | 12/2005 |
| WO | 03/070292 A1 | 8/2003 |

OTHER PUBLICATIONS

International Search Report from PCT/US2008/051059 dated Jun. 20, 2008.

Ahn, D. et al., "Craniofacial Skeletal Fixation Using Biodegradable Plates and Cyanoacrylate Glue", *Plastic and Reconstructive Surgery*, pp. 1508-1517, 1996.

Amarante, M. et al., "Cyanoacrylate Fixation of the Craniofacial Skeleton: An Experimental Study", *Plastic and Reconstructive Surgery*, pp. 639-646, 1995.

Gossain, A. et al., "Biomechanical Evaluation of Titanium, Biodegradable Plate and Screw, and Cyanoacrylate Glue Fixation Systems in Craniofacial Surgery", *Plastic and Reconstructive Surgery*, pp. 582-591, 1997.

Japanese Office Action issued Jan. 7, 2014 for Application No. 2009-546474 (7 Pages).

Li et al., Further investigations on the hydrolytic degradation of poly (DL-lactide). Biomaterials. Jan. 1999;20(1):35-44.

Cai et al., J Polym Sci Polym Phys. 1996;34:2701-8.

Li et al., Structure-property relationships in the case of the degradation of massive poly(?-hydroxy acids) in aqueous media. J Mater Sci : Mater Med. 1990;1(4):198-206.

European Search Report for Application No. 08705931.7, issued Nov. 26, 2012.

Japanese Office Action issued Dec. 25, 2012 for Application No. 2009-546474 (3 Pages).

Li et al., In vitro evaluation of biodegradable poly(butylene succinate) as a novel biomaterial. Macromol Biosci. May 23, 2005;5(5):433-40.

Xu et al., Poly(butylene succinate) and its copolymers: research, development and industrialization. Biotechnol J. Nov. 2010;5(11):1149-63.

Daniels et al., Mechanical Properties of Biodegradable Polymers and Composites Proposed for Internal Fixation of Bone, J. of Applied Biomaterials, 1990.

* cited by examiner

BIODEGRADABLE BONE PLATES AND BONDING SYSTEMS

PRIORITY OF THE INVENTION

The present invention claims priority to U.S. Provisional Application No. 60/885,303 filed Jan. 17, 2007 entitled "Novel Biodegradable Bone Plates and Bonding Systems."

FIELD OF THE INVENTION

The invention relates to novel internal fixation devices, such as bone plates, generally and novel craniomaxillofacial bone plates more specifically and systems for bonding the same.

BACKGROUND OF THE INVENTION

Internal fixation devices, such as those used in craniomaxillofacial surgery historically have been made of various materials including metals such as titanium. Poly(lactic acid) or polylactide polymers have also been successfully utilized as medical implants due to their biocompatibility with biological tissues; degradability in vitro and in vivo; and good mechanical properties. Extensive work has been carried out by several investigators in understanding the morphological properties of poly(L-lactic acid) [PLLA]. In particular, considerable progress has been made in elucidating the crystalline structure (4) and crystallization kinetics of PLLA. Recently, detailed studies were carried out to investigate the influence of physical aging on the viscoelastic behavior of PLLA, and the effects of water sorption on the internal motions in PLLA and other related polymers. The influence of morphology (crystalline and amorphous) on the degradation of PLLA was conducted in aqueous media for periods up to 2 years. It was determined from this study that the highly crystalline residues appear to be very resistant to degradation, and that degradation proceeds more rapidly in the center than at the surface for both the crystalline and the amorphous specimens. (S. Li and S. McCarthy, *Biomaterials*, 20, 35, 1999. H. Cai, V. Dave, R. A. Gross, S. McCarthy, J. Polym. Sci., Polymer Physics, 40, pgs. 2701-2708, (1996). S. Li, H. Garreau and M. Vert, *J. Mater. Sci.: Mater. Med.,* 1(4), 198, 1990).)

Recently, internal fixation devices fabricated from biodegradable polymers such as poly(lactic-co-glycolide) (PLGA) have become popular. Fixation devices made of these types of materials have advantages over older metallic devices: they do not corrode; they can be constructed in such a way as to avoid stress yielding; and they are resorbable which obviates the need to remove the devices. Further, these devices are specifically designed for use in the pediatric patient population as their resorption eliminates any adverse, restrictive effect that permanent plates would impose on craniomaxillofacial growth and development.

Craniofacial surgery is performed routinely in the United States and around the world for numerous problems involving the skull. These include craniosynostosis (premature fusion of the cranial sutures); skull deformities associated with syndromes such as Crouzon Syndrome and Apert Syndrome; skull deformities resulting from the resection of both benign and malignant tumors; and complex craniofacial trauma involving the bones of the face and skull.

Resorbable plates and screws are, for example, routinely utilized in the pediatric population for the stabilization of bones during reconstruction in each of these scenarios. The use of screws to secure plates requires additional cumbersome power equipment that necessitates additional operating room staff training and cost as well as additional surgical time that increases the cost of the operating room, anesthesia time and surgical time. A product that can eliminate the need for screws but still permit satisfactory bony stabilization for craniofacial reconstruction would yield a great medical advance in the field of craniofacial surgery and pediatric care by (1) simplifying and expediting the intra-operative application of plates to the skull, and (2) making power equipment for drilling holes for the use of screws entirely unnecessary At present, several types of craniofacial surgery plating systems are currently commercially available. Those made by Stryker-Leibinger and Synthes include titanium systems as well as resorbable polymer-based systems. The resorbable systems require fixation with resorbable screws. Based on the polymers used in these systems, resorption of plates and screws occurs approximately 2 years following placement. A new product produced by KLS Martin is the only internal fixation product that does not use screws, per se, for fixation. The product, Sonic Weld™, instead of using screws requires that a tack be applied directly into a drilled hole. An ultrasonic device then melts the resorbable tack within the hole. Thus, no actual screwing takes place but the material is melted into the hole and secures the plate in that fashion. Equipment is still required to facilitate drilling of these holes for placement of these tacks. This method has been criticized for the unknown effect of the material permeating the bony trebeculae. Furthermore, such a method still requires the use of power equipment during surgery.

Further, an internal fixation system that contributes to the quality of bone healing by the administration of growth factors or other biologically-active molecules, would be an invaluable addition to the armamentarium of the reconstructive craniofacial surgeon. The invention described herein can be impregnated with such biologically-active (bioactive) molecules due to the nature of the co-continuous polymers utilized which permit introduction of pores into the actual plate structure, yielding a porous, bioactive plate. Further, the size of these pores, and hence the degree of porosity, can be selectively controlled to permit molecules of varying sizes to be impregnated into the structure of these plates. As such, the biodegradable, resorbable bone plates described in this invention are the first such porous plates to be utilized as craniomaxillofacial bone plates.

Introduction of pores to the resorbable plating system described in this invention permits more rapid resorption of the plates. As bone healing occurs fully within 6 weeks following bone fixation during reconstructive craniofacial surgery for the management of either congenital deformities or fractures, fixation systems are not required beyond this time point. Plate porosity permits controlled plate resorption within 3-6 months following placement, considerably earlier than other resorbable plating systems.

SUMMARY OF THE INVENTION

In one aspect the invention comprises an internal fixation device comprised of a polymer blend, the polymer blend comprising a first polymer and a second polymer. The first polymer comprises PLA or a PLA-based polymer or co-polymer and the second polymer comprises a polyester-based polymer or co-polymer. In one embodiment of the invention the second polymer is comprised of a flexible, compatible, biodegradable polymer such as Bionolle, Ecoflex, or Dioxanone.

The internal fixation device of the invention can comprise any number of internal medical devices, but is preferably a bone plate. In a preferred embodiment, the internal fixation device is a bone plate used for craniomaxillofacial surgery. Alternative embodiments include, but are not limited to, bone plates for use in treating hand fractures and plates used in conjunction with osteotomies.

The polymer blend used to make the internal fixation device is preferably about at least 10% PLA. In a preferred embodiment, the internal fixation devices of the invention are comprised of a polymer blend of about 80% PLA and of about 20% Ecoflex.

The internal fixation devices of the invention can be made as a single plate and affixed to human tissue using any number of conventional fixation devices or techniques including screws and adhesives. Preferably, the internal fixation devices of the invention are affixed to tissue using the hot melt polymer blend that is disclosed and claimed herein.

Alternatively, the internal fixation devices of the invention can be made as multiple components and the components can then be assembled into a complete fixation device either prior to or during internal implantation. The components may be assembled using any number of conventional fixation devices or techniques including screws and adhesives, such as cyanoacrylate. Preferably, however, the internal fixation devices of the invention are affixed to tissue using the hot melt polymer blend that is disclosed and claimed herein The invention also comprises a novel polymer-based adhesive blend comprising a first polymer and a second polymer wherein the first polymer comprises PLA and the second polymer comprises a polyester-based polymer. In a preferred embodiment the novel polymer-based adhesive blend of the invention is a hot melt adhesive. In a more preferred embodiment, the novel polymer-based adhesive blend of the invention comprises a blend of PLA and Ecoflex.

In one aspect of the invention the adhesive blend comprises at least 10% PLA. In other aspects of the adhesive blend of the invention comprises at least 20% PLA, at least 30% PLA, at least 40% PLA at least 50% PLA, at least 50% PLA, at least 60% PLA, at least 70% PLA, at least 80% PLA. In one embodiment the polymer-based adhesive blend of the invention is comprised of about 50% PLA and of about 50% of a polyester-based polymer or co-polymer. In one preferred embodiment, the polyester-based polymer is comprised of Ecoflex.

The invention also comprises a method for processing the internal fixation devices of the invention for surgery, comprising obtaining the device, sterilizing the device; and storing the device in a sterile container. Preferred methods of sterilization include: gamma irradiation, ethylene oxide, e-beam, and ultraviolet light.

The invention also contemplates a method for bonding an internal fixation device to human tissue comprising applying the polymer-based adhesive blend described above to either the human tissue or the internal fixation device, heating the polymer blend, and affixing the internal fixation device to the human tissue. In one aspect of the invention the internal fixation device is the internal fixation device described above comprised of a polymer blend of PLA and a polyester-based polymer. In one embodiment of the invention the internal fixation device is a bone plate.

The invention also contemplates a method for constructing plates that are selectively porous, a quality that permits impregnation of the plates with biologically-active (bioactive) molecules while also facilitating earlier resorption of the plates compared with existing resorbable plating systems The invention also contemplates a method of stabilizing a wound or fracture at a site of interest by directly applying the novel adhesive blend disclosed herein to the site of interest without the use of an external fixation device and allowing the adhesive to cure or harden or undergo phase change so as to securely bond to the fracture or wound.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
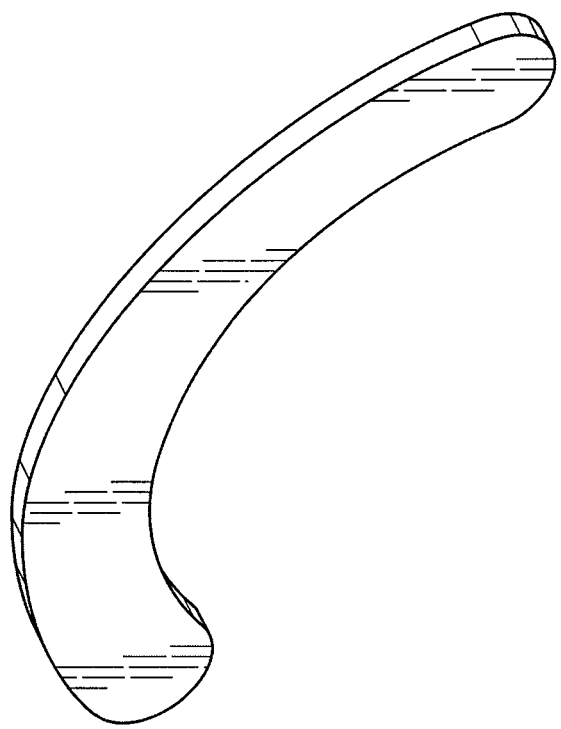
FIG. 1 is a sample design of an internal fixation device of the invention.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

Novel Implant

The invention contemplates novel biodegradable biologic implants. The implants of the invention can be any type of medical implant. In a preferred embodiment, the implants of the invention comprise bone plates and more preferably craniomaxillofacial plates for the fixation and stabilization of segments of bone of the craniomaxillofacial skeleton during reconstructive surgery. In another embodiment, the implants of the invention comprise bone plates for use in treating hand fractures. In a further embodiment, bone plates used in conjunction with osteotomies are contemplated.

The implants of the invention can be made as a unitary whole, as for example, by injection molding or may alternatively be made as components to be assembled using the bonding system or systems disclosed herein, including but not limited to cyanoacrylate, polyvinyl acetate, mixtures of polyvinyl acetate and cyanoacrylate, as well as the novel hot-melt adhesive system of the invention described below.

The novel biodegradable implants of the invention are manufactured using blends of polylactic acid (PLA)-based polymers or copolymers and polymers or co-polymers of polyesters.

More specifically the novel implants of the invention are manufactured using a biodegradable blend including a first, PLA-based polymer or copolymer, and a second polymer or copolymer including one or more polyesters, e.g., an aliphatic polyester The second polymer or copolymer can be, for example, a polybutylenesuccinate homopolymer, polybutyleneadipate homopolymer, polybutylenesuccinate-adipate copolymer, polyethylenesuccinate homopolymer, polyethyleneadipate homopolymer, or a polyethylenesuccinate-adipate copolymer, or a copolyester of an aliphatic polyester and up to 50 percent, by weight, of an aromatic polyester, such as terephthalate, as long as the overall copolyester (and second polymer) is biodegradable.

The second polymer can be present in the new biodegradable blends as a co-continuous phase with the first polymer, and at least the first or the second polymer or copolymer is present in a co-continuous phase in the blend.

Such blends are disclosed in U.S. Pat. No. 5,883,199 to McCarthy et al., which issued on Mar. 16, 1999, the disclosure of which is hereby incorporated by reference in its entirety.

Biodegradeable implants made from such materials, as compared for example to PLA, a material commonly used in maxillofacial plates, have superior tensile and mechanical properties such as stiffness, toughness, and elongation to break, as well as excellent biodegradability and aging properties.

The biodegradeable implant of the invention can be fabricated using numerous manufacturing routes. For off the shelf implant systems which offer standard sizes and shapes, many conventional processing techniques can be used, including, but not limited to injection molding, compression molding, blow molding, thermoforming, die pressing, slip casting, electrochemical machining, laser cutting, water-jet machining, electrophoretic deposition, powder injection molding, sand casting, shell mold casting, lost foam casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing spinning, and powder metallurgy compaction.

The implants can also be custom designed based on CAD models derived from medical imaging data such as MRI and CT scans, and computer driven manufacturing techniques such as, but not limited to computerized numerical controlled machining (CNC), electrodischarge maching (EDM), laminated object manufacturing (LOM), computer aided manufacturing of laminated engineering materials (CAM-LEM), stereolithography (SLA), selective laser sintering (SLS), and solid ground curing (SGC), fused deposition modeling (FDM), three dimensional printing (3DP), and Turbocasting. The pre-form can be made either directly by these CAD-based processes, or indirectly from non-functional templates made by these CAD-based processes. That is, numerous software packages are already available to convert common medical images into enhanced 3D renderings for pre-surgical visualization and planning. Depending on the file format, the rendering data can be used by service bureaus to fabricate life-size, reference prototype models to facilitate pre-surgical planning.

Various bonding systems can be used to adhere the novel implants of the invention. The systems include, but are not limited to glue-based bonding systems that use cyanoacrylate, polyvinyl acetate and mixtures of polyvinyl acetate and cyanoacrylate, as well as the novel hot-melt system described below.

Figure 2:
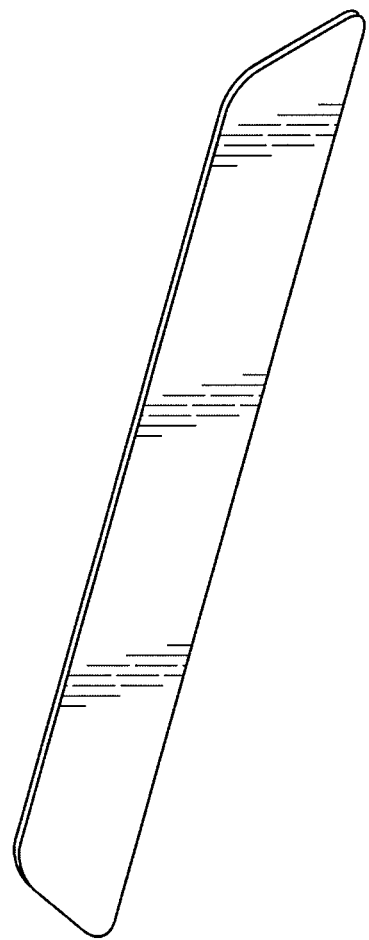
FIG. 2 is another sample design of an internal fixation device of the invention.
Figure 3:
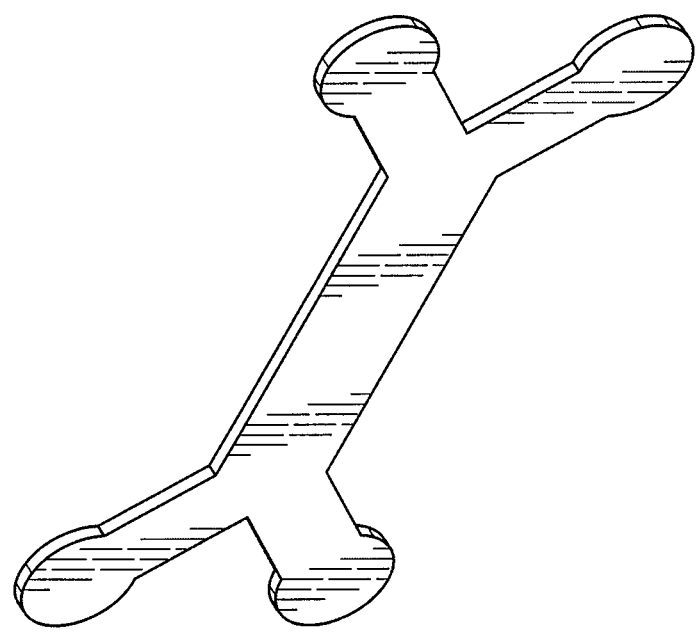
FIG. 3 is another sample design of an internal fixation device of the invention
Figure 4:
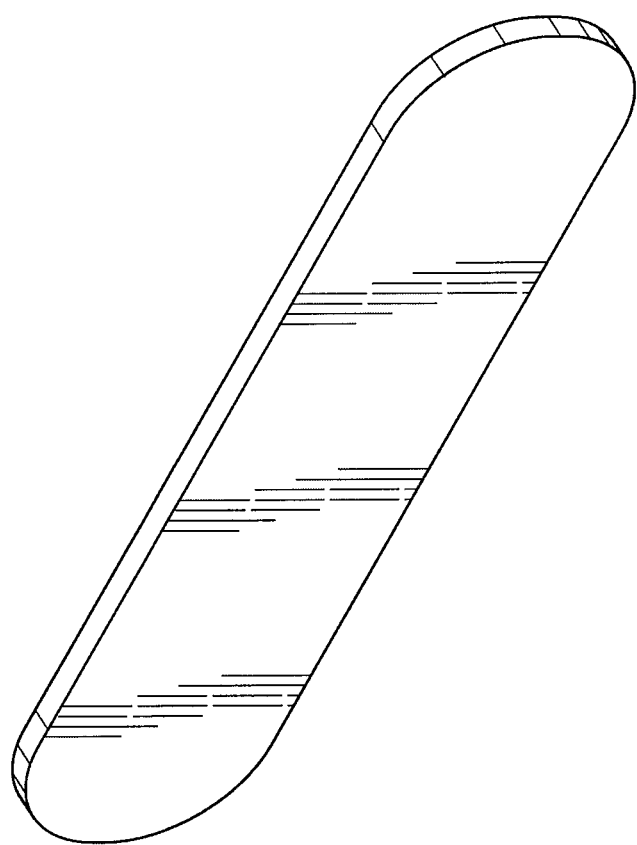
FIG. 4 is another sample design of an internal fixation device of the invention
Figure 5:
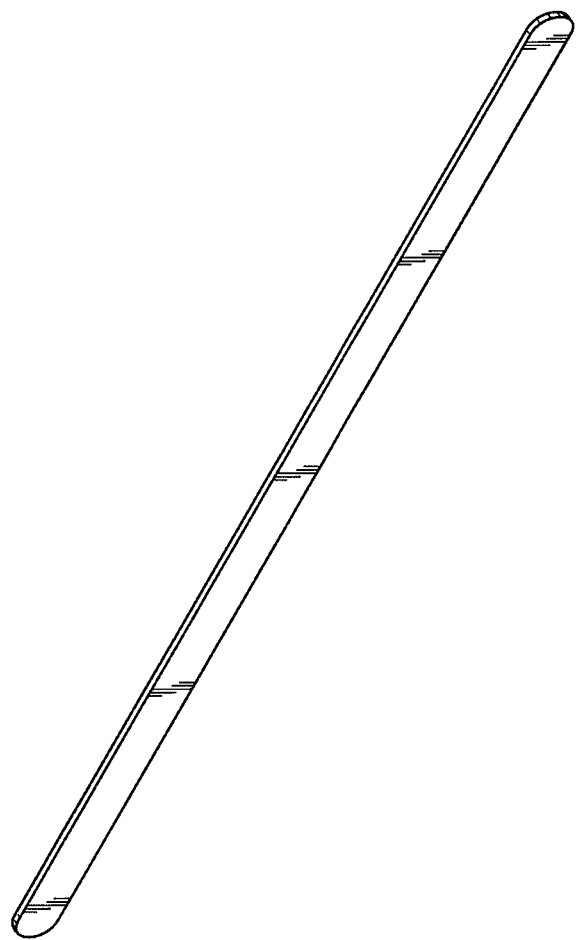
FIG. 5 is another sample design of an internal fixation device of the invention
Figure 6:
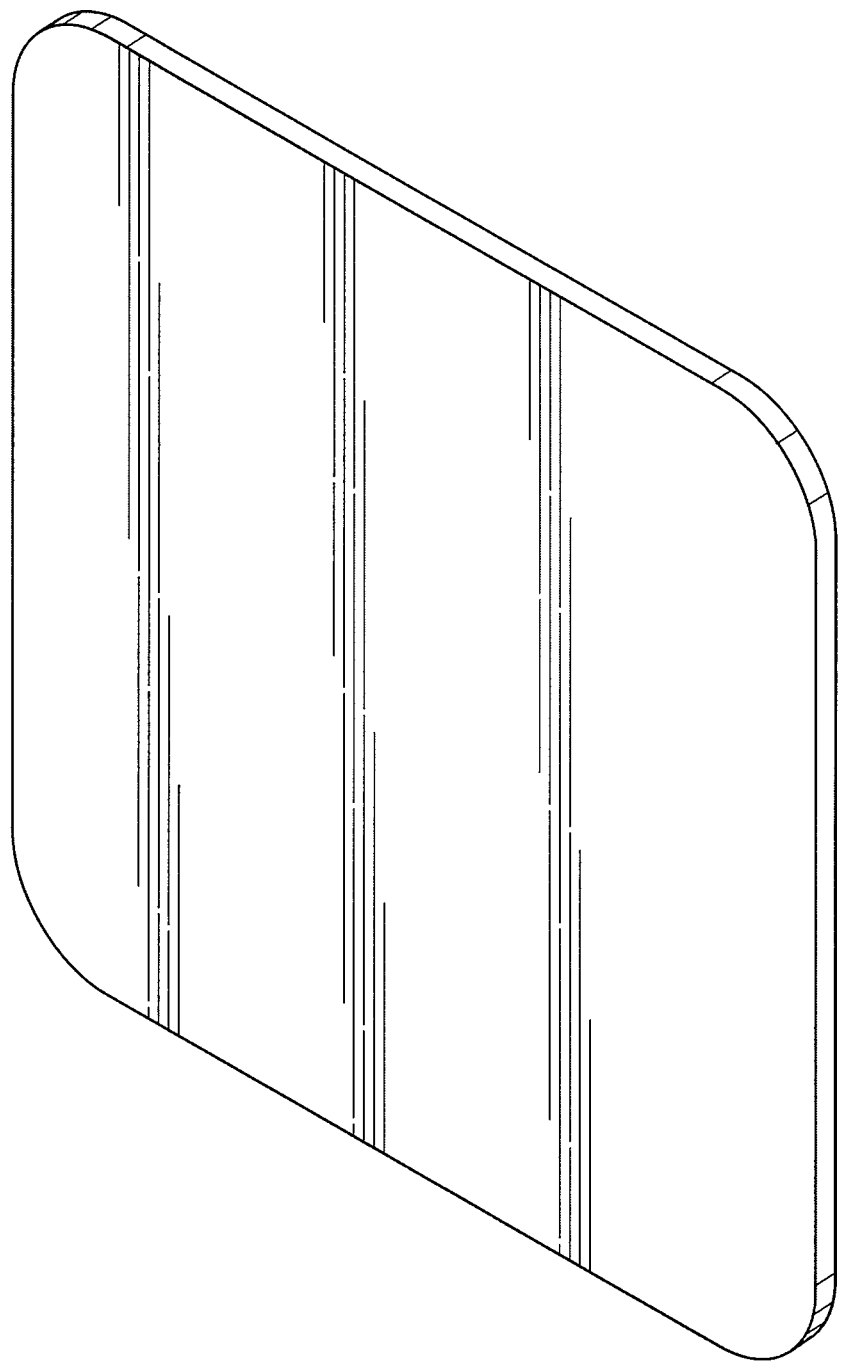
FIG. 6 is another sample design of an internal fixation device of the invention
Figure 7:
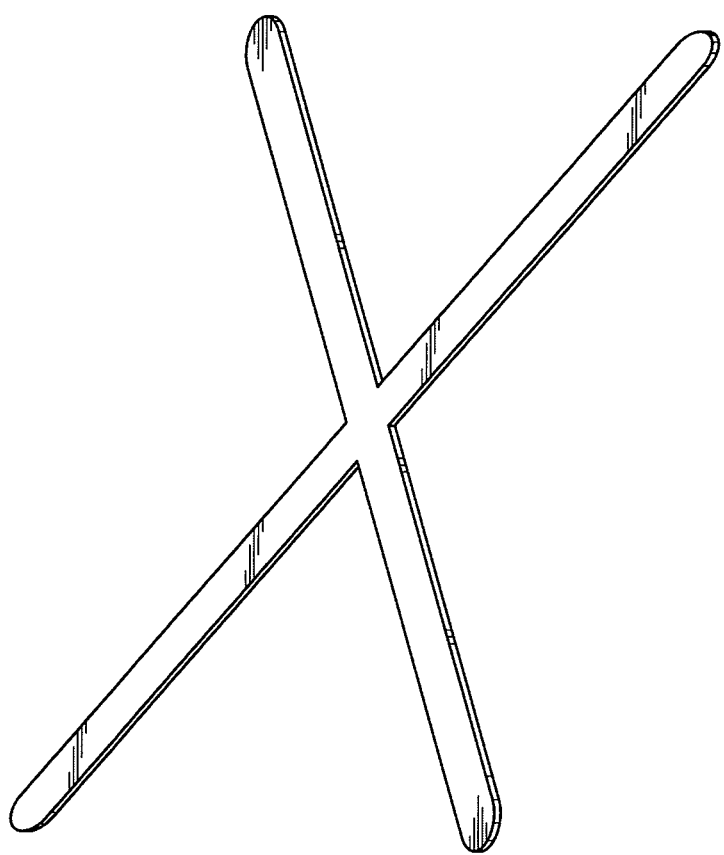
FIG. 7 is another sample design of an internal fixation device of the invention.

The novel implant of the invention can be manufactured into a variety of shapes. FIG. 1 shows a bone plate having a generally arcuate shape. FIG. 2 shows a bone plate having a generally flattened rod like shape. FIG. 3 shows yet another embodiment of the bone plates of the invention wherein the plate has a generally elongated main axis with potions proceeding at angle from the main axis. FIG. 4 shows a bone plate that is generally rectangular in shape. FIG. 5 shows an internal fixation device of the invention comprising a rod. FIG. 6 shows a bone plate that is generally square in shape. FIG. 7 depicts a bone plate that is cross-shaped.

Novel Bonding System

The invention also contemplates a novel adhesive bonding system that can be used with various biodegradable medical implants (e.g., plates) including the novel biodegradable implants disclosed above. The novel bonding system eliminates the need for screw fasteners, and thus any drilling of bony segments, while maintaining the resorption characteristics of the bone plate. Specifically, the invention contemplates a melt-adhesive system comprising a first polymer which comprises PLA or a PLA-based polymer or co-polymer and a second polymer which comprises a polyester-based polymer or co-polymer.

In one aspect of the invention this melt-adhesive (or bonding) system comprises a polymer that includes polylactic acid (PLA) or a polyester based polymer such as Ecoflex® (a commercially available biodegradable polyester from BASF) or a mixture of the two compounds.

The polyester based polymer or copolymer of the melt-adhesive system can be, for example, a polybutylenesuccinate homopolymer, polybutyleneadipate homopolymer, polybutylenesuccinate-adipate copolymer, polyethylenesuccinate homopolymer, polyethyleneadipate homopolymer, or a polyethylenesuccinate-adipate copolymer, or a copolyester of an aliphatic polyester and up to 50 percent, by weight, of an aromatic polyester, such as terephthalate, as long as the overall copolyester (and second polymer) is biodegradable.

In one embodiment of the bonding system of the invention a PLA/polyester blend is contemplated, wherein the blend is between about 10% and about 80% PLA. In another embodiment the bonding system is composed of between about 20% and about 70% PLA. In a further embodiment the bonding system is composed of between about 40% and about 60% PLA. In another embodiment of the invention a blend of about 50% PLA and about 50% Ecoflex is contemplated.

As shown in the examples, such a blend has highly improved characteristics comparable to both cyanoacrylate, a common surgical adhesive or a PLA melt alone.

Any suitable heat generating apparatus can be used to heat and soften or spot weld the material, such as a hot air gun, a small welding or soldering gun, or a Bovie tip. Also usable are lasers, which are commonly provided in operating rooms. Lasers are especially desirable because they are precise and controlled in their application, can generate sufficient heat very quickly, and cause less thermal necrosis because there is less misdirected heat. The heating operation can be done pre-operatively to form an assembly; can be done outside the body but in the operating room to customize implants at the time of surgery; or can be done during surgery, in the body, when the bond is needed within the human body.

Uses of Novel Bonding System

As well as being used as a bonding agent in both conventional stabilization systems (bone plates and pins) as well as in conjunction with the novel bone plates of the invention, the bonding system of the invention may be useful in a number of situations where these systems are not feasible. Hence the invention also contemplates a plate-less bonding system comprised of the adhesive blend of the invention. In particular, the invention contemplates the direct application of the adhesive blend of the invention to the site of interest (generally a bone fracture or osteotomy) without the use of another fixation means such as a plate, pin or screw.

There are a number of advantages in using such a plate-less bonding technique including: the elimination of the need for plates and instrumentation as well as simplification of technique for operating room personnel; the elimination of the need for subsequent plate removal that is often necessary due to the plate's interference with extensor tendon function in the hand or its palpability beneath the scalp; and the reduction of operating room time.

By way of example, the bonding system of the invention can be used in place of a plate, pin or screw, such as certain types of hand and craniofacial fractures where bone plates may be contraindicated such as: hand fractures close to the articular surface where there may be inadequate room for placement of a plate; hand fractures close to the ephiphyseal growth plate in children where there is inadequate room for plate placement; non-displaced or minimally displaced hand and craniofacial fractures requiring stabilization, the fractures being in locations where placement of plates is not feasible; severely comminuted fractures where stabilization by pure bonding (without plates) is the only option; and hand fractures in the elderly patient in whom plate placement may not be feasible due to confounding medical issues such as inadequate bone stock amenable to other modalities.

EXAMPLES

Compression Molded Bone Plate Preparation

Material Used
a) Polylactic acid (commercially available biodegradable aliphatic polyesters)
b) Bionolle (commercially available aliphatic succinate-adipate polyesters)
c) Ecoflex (Commercially available biodegradable polyesters by BASF)
d) Aluminum sheets of various thicknesses (1, 1.5, and 2 mm) for compression molding.
e) Commercially available 0.5 mm thickness steel mold
Procedure:
Molding: Polylactic acid polymer pellets were dried in a vacuum oven for 24 hours at 40° C. The dried polymer pellets were placed in the mold between 25% glass filled Teflon coating sheets (for smoother surfaces). The compression molding plates were preheated at 175° C. for 45 minutes. It was assured that the molds share the same temperature to that of the compressing plates. The mold was placed between the plates of compression molder and preheated for 5 minutes. Before applying the entire pressure the mold was evacuated 2 to 3 times to remove any trapped air or gases between the pallets. A pressure of 5 MPa was applied for 3 minutes. This step was followed by removal of mold plates and cooling them in air at room temperature.

Blends of PLA with Ecoflex with the ratio 80:20 and 50:50 were prepared in melt blender (HAKKE Rheocord, TYP-557-0029, capacity 60 grams by weight). The resin was dried for 6 hours at 60° C. in the vacuum oven. The blending temperature was selected as the melt temperature for the resins (175° C.). The rpm was set at 40±0.5. The cycle time was set as 3 minutes.

Compression molded plates of 2 mm thickness (68 mm×128 mm) were prepared. Similar procedure as for PLA compression molded bone plates was followed. The compression molded bone plates were then cut into strips of 7.5 mm×68 mm to be attached to fresh bone specimen using adhesion techniques Bone Specimen Preparation:
Fresh beef femurs were obtained from a local butcher. On an average the femurs provided were 180 mm×53 mm×6 mm in dimension. These femurs were then peeled of their skin and cut into 62 mm×9 mm×4 mm strips. The strips were burred from the non testing end for the ease of mounting on the Instron Tensile Testing machine. The strips were quarantined in a moist environment to keep them fresh Experimentation
Two kinds of adhesion experimentations were performed:
a) Adhesion using liquid adhesive
b) Adhesion using melt adhesive
Adhesion Using Glue:
Material Used:
i) cyanoacrylate
ii) polyvinyl acetate
iii) Mixture of cyanoacrylate and polyvinyl acetate
Procedure for Cyanoacrylate:
The bone specimens were wiped using Kimwipes® and a drop of cyanoacrylate was applied on the surface of bone. The bone plate specimens were brought in contact with the bone parts carrying cyanoacrylate. The glued section between bone and bone plate was kept under thumb pressure for the initial minute. Then the tensile testing was preformed.
Procedure for Polyvinyl Acetate:
Similar adhesion technique was performed for polyvinyl acetate liquid adhesive.
Procedure for cyanoacrylate and polyvinyl acetate mixture:
The bone specimens were wiped using Kimwipes® and a drop of cyanoacrylate was applied on the surface of bone. A drop of polyvinyl acetate was applied on the bone plate specimen. Both, the bone plate and bone specimen sections carrying glue were brought in contact with each other and thumb pressure was applied for 1 minute.
Adhesion using Melt:
Material Used:
i) PLA melt
ii) Ecoflex Melt
iii) 50:50 blend of PLA and Ecoflex
Procedure for PLA Melt:
The bone specimens were wiped using Kimwipes® and PLA melt was dropped on the surface of bone. The bone plate specimens were kept in contact with the melt (on the bone) and pressed a couple of times for the first minute. This was followed by tensile testing of the adhered samples. During the duration between samples preparation and testing the samples were physically aged at room temperature and atmospheric pressure.
Procedure for Ecoflex Melt and PLA/Ecoflex Blend
Similar melt bonding procedure, as for PLA melt, was performed using Ecoflex and Blend melt.
Testing Procedure:
Tensile testing was done according to ASTM D 882 with the modifications in the sample length between the grip separation and the grip separation rate.
Specifically tensile testing was performed by using Tensile Testing machine, model number 6025 at grip separation rate of 2.0 inches/minute, and a load cell of 50 kN.
The machine was operated in tension mode. The tensile properties of the adhesive strengths were obtained with the time interval of 30 minutes and 1 hour after making the samples. During this interim time period between preparing and testing the samples were physically aged at room temperature and atmospheric pressure.
The strength of the bond was determined from the load required to separate bone-plate from the bone. The stiffness of the blends was determined from the slope of the initial linear portion of the stress-strain curve. Stress was measured as the nominal stress defined as force per unit area. Strain and elongation are used as synonymous terms, and they were measured as percent change in length per unit length of a sample.

The toughness of the blends, which can be defined as the tensile energy to break according to ASTM D 822, was measured according to ASTM D 822 by integrating the area under the stress-strain curve.

The load cell of Instron tester was balanced, zeroed, and calibrated for measuring recording force. The rectangular test specimen was placed in the grips of the Instron testing machine, taking care to align the long axis of the specimen with an imaginary line joining the points if attachment of the grips to the machine. The grips were tightened evenly and firmly to the degree necessary to minimize slipping of the specimen during tests. The Instron machine was started and stress versus grip separation was recorded.

Tensile stress (nominal) was calculated by dividing the load by the original minimum cross-section area of the specimen in the loading direction. The modulus value was determined from the initial slope of the stress-strain curve. Tensile strength (nominal) at break was calculated in the same way as tensile stress except that the load at break was used in place of maximum load.

Tensile stress at break and energy at break curves for different combinations of glue and melt are represented in Table 1 and Table 2 respectively. These blends were physically aged to determine the effect of time on melt properties. Increase in bond strength was exhibited with time. Increase in tensile stress at break and energy at break for 60 minute samples indicates that the setting time for the bond is around 60 minutes.

Maximum Load was calculated recorded from the Instron machine.

Results:

Bone plates used for all the testing were made of 80:20 PLA/Ecoflex blend. During tensile testing it was observed that bone plates made of pure PLA were very brittle and had lesser mechanical properties as compared to the adhesive bond resulting in fracture of the plate before the adhesive bond fails. 20% by weight of Ecoflex increases mechanical properties of the bone plate, making them stronger than the adhesive bond under investigation.

Adhesion phenomenon using cyanoacrylate as an adhesive required 45 minutes (approximately) for reacting. Thus there was an increase in adhesive strength observed between samples aged 30 minutes and 1 hour. Furthermore, setting time, described as the duration before which the samples will fall apart in their own weight, was observed to be 10 minutes.

Adhesion phenomenon using polyvinyl acetate required more than 2 hours (some samples were still wet after 2 hours of glue application) for drying. There was an increase in adhesive properties observed when the samples were aged from 30 minutes to 1 hour. The setting time was observed to be more than 40 minutes. This could explain the erratic readings from the testing of samples aged 30 minutes.

Adhesion phenomenon using a blend of cyanoacrylate and polyvinyl acetate required relatively shorter setting time, less than 1 minute. However, an increase in adhesive properties between samples, aged 30 minutes and 1 hour, showed that the drying time for the mixture of glue was more than pure cyanoacrylate samples and less than pure polyvinyl acetate samples.

The PLA melt required less than 3 minutes of setting time. Little increase in bonding properties over time was observed; proving that PLA melt adhesion development time is faster than cyanoacrylate. PLA melt showed the highest tensile stress at break as compared to all the other adhesive agents under investigation. Furthermore, it was observed that PLA melt sticks better to bone plate than the bone and the break occurs on the bone surface.

The Ecoflex melt required less than 3 minutes of setting time, similar to PLA melt. In this case a reduction in energy to break was observed whereas an increase in tensile modulus was observed. Furthermore, it was observed that Ecoflex melt adhesive sticks better to bone than the bone plate and the break occurs at the bone plate surface.

It was observed that the adhesion phenomenon using PLA/Ecoflex melt blend required less than 3 minutes of setting time, similar to other melts mentioned above. In this case a reduction in energy to break values over 60 minutes was observed, reflecting the presence of Ecoflex. Increase in Tensile Stress at break with time reflected presence of PLA in the blend.

Tensile Testing Results:

TABLE 1

Average data after 30 and 60 minutes of curing time for the adhesives under investigation

| Adhesives | Curing Time (min) | Energy @ Break (ft-lbs) | Tensile Stress @ Break (ksi) |
| --- | --- | --- | --- |
| cyanoacrylate + PVA blend | 30 | −0.024 | 0.016 |
| A100206 | 60 | 0.071 | 0.02 |
| cyanoacrylate | 30 | 0.101 | 0.107 |
| A100206 | 60 | 0.118 | 0.036 |
| PLA Melt | 30 | 0.106 | 0.083 |
| A101906 | 60 | 0.111 | 0.274 |
| Ecoflex Melt | 30 | 0.047 | 0.086 |
| A102206 | 60 | 0.033 | 0.128 |
| Melt Blend | 30 | 0.164 | 0.189 |
| A111906 | 60 | 0.094 | 0.215 |

Table 1 shows both the energy to break in ft-lbs of the various adhesives at two different curing times (30 and 60 minutes). The table also shows the Tensile Stress at the point of break of the bond for the various adhesives and time points Table 2 shows the maximum load (in Newtons) required to separate bone plate from bone for the various adhesive after having set for anywhere from 5-60 minutes. Superior results were shown for the PLA and Ecoflex blend melt. The PLA/Ecoflex blend was clearly superior to PLA melt or Ecoflex Melt alone and was comparable to cyanoacrylate. Results superior to cyanoacrylate were seen at 5 minutes of setting time, which approximates the amount of time the bone plate would be allowed to set in an actual surgical setting.

TABLE 2

Comparative Adhesion Strength as Measured by Maximum Load of Adhesives

| Time min | cyanoacrylate | cyanoacrylate + PVA blend | PLA melt | PLA + Ecoflex Melt | Ecoflex melt |
|---|---|---|---|---|---|
| 5 | 144.29 | 4.95 | 119.25 | 172.42 | — |
| 15 | 209.21 | 24.97 | 189.82 | 196.93 | — |
| 30 | 221.38 | 108.46 | 160.83 | 234.82 | 119.75 |
| 60 | 262.04 | 60.81 | 147.98 | 154.94 | 68.90 |

The invention claimed is:

1. A method of securing two or more segments of bone together, comprising:
applying a bioabsorbable, flowable polymer adhesive to a first bone segment of craniofacial bone, the polymer comprising a polymer blend that includes polylactic acid and a polyester or a copolymer that includes polylactic acid and a polyester, the amount of polylactic acid in the polymer blend or the copolymer being in the range of about 10% to about 80%, and the applying step including heating at least a portion of the polymer;
contacting a second bone segment of craniofacial bone to the first bone segment; and
subjecting the bone segments to a compressive force until the polymer hardens.

2. The method of claim 1, wherein the applying step includes applying energy to at least a portion of the polymer to melt at least a portion thereof.

3. The method of claim 1, wherein heating at least a portion of the polymer is performed with at least one of a laser, a hot air gun, a welding or soldering gun, and a bovie tip.

4. The method of claim 1, wherein the polymer is a hot melt.

5. The method of claim 1, wherein the absorbable adhesive polymer is a polymer blend of about 50% polylactic acid and about 50% polyester.

6. The method of claim 1, wherein the polyester is selected from the group consisting of polybutylenesuccinate homopolymer, popolybutyleneadipate homopolymer, polybutylenesuccinate-adipate copolymer, polyethylenesuccinate homopolymer, polyethyleneadipate homopolymer, polyethylenesuccinate-adipate copolymer, or a copolyester of an aliphatic polyester and an aromatic polyester.

7. A method for bonding tissue, comprising:
melting a bioabsorbable polymer adhesive, the polymer adhesive comprising a blend or copolymer of a polymer that includes polylactic acid and a polymer that includes polyester, the amount of polylactic acid in the blend or copolymer being in the range of about 10% to about 80%, the melting step including heating at least a portion of the polymer;
applying the melted polymer adhesive onto at least one bone tissue segment associated with craniofacial bone to be fixed such that the melted polymer contacts the at least one bone tissue segment; and
affixing the bone tissue segment to at least one other portion of bone tissue associated with craniofacial bone without the use of a mechanical fixation device.

8. The method of claim 7, wherein heating at least a portion of the polymer is performed with at least one of a laser, a hot air gun, a welding or soldering gun, and a bovie tip.

9. The method of claim 7, wherein the absorbable adhesive polymer is affixed to bone without drilling or perforating the bone.

10. The method of claim 7, wherein the amount of polymer that includes polyester is in the range of about 20% to about 90% of the blend or copolymer.

11. The method of claim 7, wherein the polymer that includes polylactic acid and the polymer that includes polyester are present in a ratio of about 50:50.

12. The method of claim 7, wherein the polyester is selected from the group consisting of polybutylenesuccinate homopolymer, popolybutyleneadipate homopolymer, polybutylenesuccinate-adipate copolymer, polyethylenesuccinate homopolymer, polyethyleneadipate homopolymer, polyethylenesuccinate-adipate copolymer, or a copolyester of an aliphatic polyester and an aromatic polyester.

* * * * *